United States Patent [19]

Syrinek

[11] Patent Number: 4,902,824

[45] Date of Patent: Feb. 20, 1990

[54] DISPERSANT FOR VINYL ACETATE UNIT FOULING

[75] Inventor: Allen R. Syrinek, Richmond, Tex.

[73] Assignee: Nalco Chemical Company, Naperville, Ill.

[21] Appl. No.: 191,641

[22] Filed: May 9, 1988

[51] Int. Cl.$^4$ .............................................. C07C 67/48
[52] U.S. Cl. .................................. 560/248; 560/261; 526/75; 252/363.5
[58] Field of Search ................... 560/248, 261; 526/75; 514/553, 555, 554, 556, 557; 252/363.5; 260/503, 505 R, 505 A, 513 R, 513 N

[56] References Cited

U.S. PATENT DOCUMENTS

| | | | |
|---|---|---|---|
| 2,684,980 | 7/1954 | Mawer | 560/261 |
| 2,784,149 | 3/1957 | Dorn et al. | 560/248 X |

FOREIGN PATENT DOCUMENTS 0046701  4/1979  Japan .................................. 560/248

OTHER PUBLICATIONS

Hackh's Chemical Dictionary, J. Grant (ed.), McGraw-Hill, Inc., 646 (1969).

*Primary Examiner*—Joseph L. Schofer
*Assistant Examiner*—Fred M. Teskin
*Attorney, Agent, or Firm*—John G. Premo; Donald G. Epple; Anthony L. Cupoli

[57] ABSTRACT

A dispersant for vinyl acetate process streams has been found, which dispersant acts as an antifoulant, preventing formation of fouling tars, polymers, debris, and the like, in the process streams involved in the manufacture of vinyl acetate monomer. The antifoulant/dispersant is primarily composed of hydrocarbonaceous sulfonic acids which may optionally be admixed organic polar solvents and tall oil fatty acids.

10 Claims, No Drawings

DISPERSANT FOR VINYL ACETATE UNIT FOULING

Vinyl acetate monomer is manufactured by three separate processes around the world. These processes include the reaction of acetic acid with ethylene in the presence of oxygen, the reaction of acetic acid with acetylene, and the reaction of acetaldehyde with acetic anhydride. Each of these processes are catalyzed by various types of metallic catalysts, e.g. palladium catalysts may be used in the reaction of ethylene with acetic acid and oxygen under the conditions of that reaction sequence.

After these reactions are run in each of these processes, the vinyl acetate formed is separated by a series of varying processes ranging from distillation, phase separations, azeotropic distillations, varying washing steps and absorption, desorption steps, steam distillations, solid/liquid phase separations, acid stripping and recovery processes involving distillations and the like, and various other processes known to function in the manufacture of this commercially important vinyl acetate monomer.

In the operation of these various processes for the manufacture and recovery of vinyl acetate monomer, varying types of equipment are used, such vinyl acetate monomer equipment including, but not limited to, distillation towers, process lines, varying and pumps, storage and knock out vessels, phase separation equipment, surge drums, condensors, demisters and heat exchangers, and such other equipment as necessary to manufacture vinyl acetate monomer and to recover the monomer and recycle unused reactants for reuse.

In the process of operating a manufacturing plant which recovers vinyl acetate monomer as its primary product, the operations of such a plant can be inhibited when foulants, residues, polymers, highly oxidized organics, dirt, sand and similar residues are caught up in the process streams and equipment, and deposited thereon, causing foulants to form and inhibiting the proper operation of such process equipment.

It would therefore be an advance in the art if one could simply add an effective amount of an antifoulant to such vinyl acetate monomer process equipment, so as to minimize or eliminate the possibility of such foulants forming and inhibiting the ability to achieve maximum use of the vinyl acetate monomer process equipment.

THE INVENTION

I have discovered an antifoulant for use in vinyl acetate monomer process equipment. I have also discovered a method of inhibiting the formation of foulants and residues, gums and precipitates, polymeric tars and other highly oxidized carbonaceous tars which can be formed in the process of manufacture and recovery of vinyl acetate monomer.

My method of inhibiting the formation of foulants and gums in vinyl acetate monomer process equipment comprises adding to the liquid or gaseous phases passing through, or stored in such vinyl acetate monomer process equipment, an effective antifouling amount of a dispersant which is stable in the environment within a vinyl acetate monomer process and is neutral to the equipment used for the manufacture of this monomer.

The dispersant which has been found that meets all of these requirements, i.e. a dispersant that can inhibit the fouling caused by polymeric tars, residues, highly oxidized carbonaceous tars and debris, and similar foulants as described above, while being compatible with the environment and chemicals used to manufacture vinyl acetate, without causing difficulties in the manufacture of such monomer, are primarily those dispersants which are alkyl sulfonic acids. These alkyl sulfonic acids are exemplified by such materials as dodecylbenzene sulfonic acid, dioctyl sulfosuccinic acid, and similar materials, such as methane sulfonic acid and the like. These sulfonic acids may be used as is, or may be formulated in a compatible solvent, and may include, optionally, other dispersants, other surfactants, antifoaming agents, corrosion inhibitors, and similar ingredients.

The antifoulant formulation preferably used is one that contains dodecylbenzene sulfonic acid, and/or its salts, optionally in combination with a tall oil fatty acid admixed and/or dissolved in an organic polar solvent, such a butyl cellosolve, an alkyl capped diether material available in commerce.

These antifoulants can contain from about 20 to about 100 weight percent alkyl sulfonic acid, preferably dodecylbenzene sulfonic acid, from about 0 to about 50 weight percent polar solvent, preferably butyl cellosolve, and from about 0 to about 25 weight percent tall oil fatty acids.

In addition, the dodecylbenzene sulfonic acid may be present as its salts, particularly its quaternary ammonium or amine salts by neutralizing the sulfonic acid with various bases or with various amines, including polyamines and the like.

In addition to the dodecylbenzene sulfonic acid, other hydrocarbonaceous sulfonic acids may be used in my invention. These sulfonic acids may be alkyl sulfonic acids which can include, but are not limited to, such organic sulfonic acids as toluene sulfonic acid, methane sulfonic acid, dodecyl sulfo succinic anhydride, dodecyl sulfosuccinic acid, and dioctyl sulfosuccinate. Representative of these sulfonic acids are those having the structure:

wherein

R is a hydrocarbonaceous group chosen from linear or branched alkyl groups, aromatic, cyclic, alkaryl, aralkyl, or alkenyl groups, and mixtures thereof; M is H alkali metals, alkaline earth metals, ammonium cations, alkylamine cations, quaternary amine cations, and the like, or mixtures thereof; and n ranges from about 1 to about 6, preferably between about 1–4, and most preferably is 1–2.

Also included in such effective sulfonic acids are structures which include alkyl aromatic sulfonic acids or alkyl naphthenic sulfonic acids, as will be described in detail hereafter.

The tall oil fatty acids normally contain from 8–30 carbon atoms, and are also products of tall oil distillation and separations known in the art. The tall oil fatty acids include, preferably, oleic acid and/or linoleic acids, or mixtures thereof.

The organic polar solvents to be used are solvents such as butyl cellosolve or any of the ethylene oxide based cellosolve capped ether solvents, and may also include such organic polar solvents as the diethyl ether of tetraethylene glycol, polyethylene and polypropylene oxide alkyl ethers, and generally may also include ketonic solvents, such as acetone or ester solvents, such as ethyl acetate, or ether solvents, such as diethyl ether or butyl cellosolve. In addition, other polar solvents that also function include certain organic acids, such as acetic acid, or such other polar solvents such as diacetone alcohol, linear alkyl and branched alkyl alcohols, such as propanol, isoprpanol, t-butanol alcohol, and the like. Admixtures of these polar solvents may also be used. It is preferred that the solvent be essentially free of water.

Tall oil fatty acids are described in the art as being obtained as a by-product of the wood pulp industry, and contains rosin acids, oleic and linoleic acid, long chain alcohols and small amounts of sterols, especially phytosterol. These tall oil fatty acids are particularly, when distilled and purified, commonly described as containing oleic and linoleic acids and mixtures thereof.

To better describe my invention, the following examples will be presented:

A dispersancy test was used to compare the relative effectiveness of candidate antifoulants. In this dispersancy test, non-solvent was added to a solution of polymeric tars at such a concentration that precipitation occurred after a short time. Dispersants are added and time to precipitation was recorded. Effectiveness of dispersancy was determined by how long the dispersant kept the polymeric tars in solution. This is a relative comparison between dispersants. It simulates what happens in a distillation unit as solvent is being removed to cause precipitation.

A 1 ml portion of the bottoms stream from the acetic acid reclaiming section of a vinyl acetate plant in Southwest United States was diluted with 99 mls of the solvent stream prior to acetic acid stripping. The bottoms stream contained acetic acid, oligomers of vinyl acetate, by products and side reaction products of the vinyl acetate manufacturing process, and similar ingredients including tars, residues, and the like. This sample contained 11.9 wt% residue after evaporation. The other solvent stream containing mostly acetic acid. This was done to make a dilute stock solution of polymeric tars. A 3.5 ml portion of the stock solution was placed in a 2 dram vial and treated with dispersant. A 2 ml portion of hexane, a non-solvent for the polymeric tars, was added to the vial. Then the vial was capped and inverted several times to insure mixing. The vial was allowed to sit and appearance of the solution checked every 10 minutes. Blanks (no dispersant) generally precipitate after 20 minutes. However, a blank was run with each set of tests. Generally no more than 8 samples were run at a time in order to limit time lag between samples to less than 30 sec. A stock solution could probably be made by solubilizing polymeric tar residue in acetone or acetic acid, but to better simulate plant situation, solvent streams were used,. Hexane was chosen as the non-solvent since this is what is used for a similar dispersancy test for asphaltenes. Isopropanol also worked as a non-solvent. In Table 1, the dispersancy data is given for formulations which contain varying amounts of active ingredients. The blank in Table 1 is simply the stock solution with no antifoulant. As can be seen, when the sample is originally taken, after obtaining temperature equilibrium in the dispersing test equipment, it is initially clear. However, after 10 minutes it has developed a haze and after 20 minutes, a floc has been formed which, in the operating units, would cause fouling, tar build-up, and the problems that this invention solves.

TABLE I

| CHEMICAL | CONC. (ppm) | INITIAL | 10 MIN. | 20 MIN. | 30 MIN. | 40 MIN. | 50 MIN. | 60 MIN. |
|---|---|---|---|---|---|---|---|---|
| BLANK | 0 | C | H | F | | | | |
| SOLVENT | 5000 | C | H | F | | | | |
| A | 5000 | C | C | C | C | H | H | F |
| A | 3000 | C | C | C | C | F | | |
| A | 1000 | C | C | H | F | | | |
| B | 5000 | C | C | C | C | C | C | F |
| B | 3000 | C | C | C | C | H | F | |
| B | 1000 | C | C | H | F | | | |
| C | 5000 | C | C | C | F | | | |
| D | 5000 | C | H | F | | | | |
| E | 5000 | C | H | F | | | | |
| F | 500 | C | H | F | | | | |
| F | 50 | H | H | F | | | | |
| F | 5 | C | H | F | | | | |
| G | 5000 | C | H | F | | | | |
| G | 500 | C | C | F | | | | |
| H | 5000 | C | H | F | | | | |
| H | 500 | C | C | F | | | | |
| I | 500 | C | C | F | | | | |
| J | 5000 | F | | | | | | |
| K | 500 | F | | | | | | |
| L | 500 | F | | | | | | |
| L | 50 | C | C | F | | | | |
| M | 5000 | C | H | H | H | H | H | F |
| $M_1$ | 5000 | C | H | H | H | H | H | F |
| $M_2$ | 5000 | C | H | H | F | | H | F |
| $M_3$ | 5000 | C | H | H | F | | | |
| N | 5000 | C | H | H | F | | | |
| P | 6000 | C | C | C | C | F | | |
| P | 3000 | C | C | C | C | F | | |
| P | 6000 | C | C | C | C | F | | |
| Q | 6000 | C | C | C | C | F | | |
| Q | 3000 | C | C | C | C | F | | |
| R | 6000 | O | | | | | | |
| R | 600 | H | O | | | | | |

TABLE I-continued

| CHEMICAL | CONC. (ppm) | INITIAL | 10 MIN. | 20 MIN. | 30 MIN. | 40 MIN. | 50 MIN. | 60 MIN. |
|---|---|---|---|---|---|---|---|---|
| S | 6000 | C | C | C | F | | | |

C = CLEAR
H = HAZY
F = FLOC
O = OILED OUT

Also, as can be seen in Table I, the organic polar solvent which in this example is butyl cellosolve, when added at 5000 ppm (parts per million) to the stock solution, has essentially no effect as an antifoulant, and is used simply as a carrier of those materials which are active in the invention.

In Table I, Formula A is dodecylbenzene sulfonic acid; Formula B is methane sulfonic acid; Formula C is toluene sulfonic acid; Formula D is dodecyl succinic anhydride; Formula E is a distilled tall oil fatty acid; Formula F is a known sulfur-free, polymethacrylate copolymers dispersant; Formula G is dodecylbenzene sulfonic acid neutralized with a heavy amine condensate product; Formula H is a mixture of PEG-4000 and PEG-400 dioleates in dipropylene glycol solvent; Formula I is a heavy amine condensate product used to neutralize an organic phosphate ester; Formula J is 70% phosphorous acid in water; Formula K is 85% phosphoric acid in water; Formula L is a low molecular weight polymer derived from reacting maleic anhydride and vinyl ether; Formulas M, $M_1$, $M_2$, and $M_3$ are various admixtures of dodecylbenzene sulfonic acid with varying amounts of butyl cellosolve and tall oil fatty acids; Formula N is a fatty acid ethoxylate; Formula P is an alkyl substituted diphenyl ether which has been sulfonated to obtain two sulfonic acid groups, one on each aromatic structure, which formula is represented by the Formula I below:

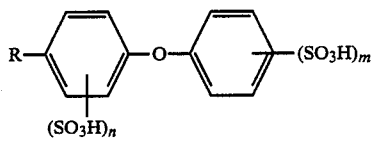

wherein
R is a linear or branched alkyl group having from 4-16 carbon atoms, and m and n range at each occurrence from 0-1 provided the sum of m+n is at least 1, and preferably 2.

Formula Q is a dialkyl substituted naphthalene sulfonic acid described in Formula II below:

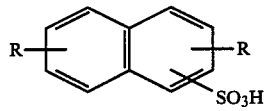

wherein
R is a linear or branched alkyl group having from 4-12 carbon atoms.

Formula S is a dioctyl sodium sulfosuccinate solution.

The alkyl sulfonic acids described above are preferred when used in the bottom streams at concentrations ranging from about 10 ppm to about 20,000 ppm, based on the weight ratios of the additive formulation to the bottom stream to which the formula is added. However, my hydrocarbonaceous sulfonic acids, or their formulations can function as antifoulants at treatment concentrations ranging from about 10–20,000 ppm, preferably beytween about 100–10,000 ppm, and most preferably, between about 1000–7500 ppm (wt. %) treatment acid based on the process stream being treated.

Also, as can be seen, although the alkyl sulfonic acids can be used as amine salts, the activities of some amines, such as the heavy amine condensate salts are not as good as the activities of the free acids. Therefore, it is most preferred to use the sulfonic acids of the instant invention as the free acid.

Having described my invention, I claim:

1. A method of inhibiting the formation of tars, gums, and foulants in vinyl acetate monomer manufacturing and recovery equipment which comprises adding to the liquid or gaseous phases contained therein an effective antifouling amount of an antifoulant, said antifoulant having the structure:

wherein;
R is a hydrocarbonaceous group having from 1–34 carbon atoms chosen from linear or branched alkyl groups, aromatic, cyclic, alkaryl, aralkyl, or alkenyl groups, alkyl diphenyl ether groups, dialkyl naphthalene groups, or mixtures thereof;
M is chosen from the group consisting of H, alkali metals, alkaline earth metals, ammonium cations, alkyl ammonium cations, or mixtures thereof; and n ranges from 1 to about 6.

2. The method of claim 1 wherein the antifoulant is chosen from the group consisting of dodecylbenzene sulfonic acid, methyl sulfonic acid, toluene sulfonic acid, alkyldiphenyl ether disulfonic acid, dialkyl napthalene sulfonic acid, dioctyl sulfosuccinic acid, or mixtures thereof.

3. The method of claim 1 or 2 wherein the antifoulant is admixed with an organic polar solvent chosen from ketones, ethers, esters, alcohols or mixtures thereof, and also contains at least 1 weight percent of tall oil fatty acids.

4. The method of claims 1 or 2 wherein the effective antifouling amount of antifoulant ranges between about 10–20,000 ppm antifoulant, based on the process stream being treated.

5. The method of claim 4 wherein the effective amount ranges between about 100–10,000 ppm antifoulant.

6. The method of claim 5 wherein the effective amount ranges from about 1000–6000 ppm antifoulant.

7. The method of claim 1 or 2 wherein the antifoulant is admixed with an organic polar solvent chosen from the group consisting of acetic acid, acetone, butyl cellusolve, ethyl acetate, diacetone alcohol, and mixtures thereof, and also contains at least 1 weight percent of tall oil fatty acid.

8. A method of inhibiting the formation of tars, gums, and foulants in vinyl acetate monomer manufacturing and recovery equipment which comprises adding to the liquid or gaseous phases contained therein an effective anti-fouling amount of an antifoulant chosen from the group consisting of toluene sulfonic acid, methane sulfonic acid, dodecylsulfosuccinic anhydride, dodecylsulfosuccinic acid, dioctyl sulfosuccinate, dodecylbenzene sulfonic acid, methane sulfonic acid, toluene sulfonic acid, dodecylsuccinic anhydride, and alkyl-substituted diphenylether which has been sulfonated to obtain two sulfonic acid groups, one on each aromatic structure, as represented in the following formula:

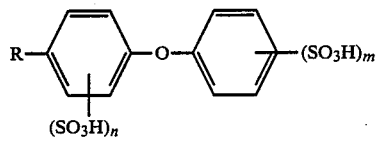

wherein
R is a linear or branched alkyl group having from 4–16 carbon atoms, and the sum of m+n is at least 2; a dialkyl substituted naphthalene sulfonic having the formula:

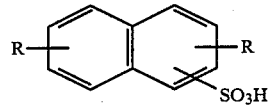

wherein
R, at each occurrence, is a linear or branched alkyl group having from 4–12 carbon atoms; and salts thereof, and mixtures thereof.

9. The method of claim 8 wherein the anti-foulant is present as a salt of an alkali metal, an alkaline earth metal, an ammonium cation, an alkyl cation, a quaternary amine cation, or mixtures thereof.

10. The method of claim 8 or 9 wherein the antifoulant is admixed with an organic polar solvent chosen from the group consisting of ketones, ethers, esters, alcohols, or mixtures thereof, and also contains at least one weight percent of tall oil fatty acids.

* * * * *